United States Patent
Asano

(10) Patent No.: US 9,322,814 B2
(45) Date of Patent: Apr. 26, 2016

(54) MASS SPECTROMETER

(75) Inventor: Natsuyo Asano, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 41 days.

(21) Appl. No.: 14/391,810

(22) PCT Filed: Apr. 12, 2012

(86) PCT No.: PCT/JP2012/059976
§ 371 (c)(1),
(2), (4) Date: Oct. 10, 2014

(87) PCT Pub. No.: WO2013/153647
PCT Pub. Date: Oct. 17, 2013

(65) Prior Publication Data
US 2015/0268203 A1   Sep. 24, 2015

(51) Int. Cl.
*G01N 30/86* (2006.01)
*G01N 30/72* (2006.01)
*H01J 49/00* (2006.01)

(52) U.S. Cl.
CPC ............ *G01N 30/8631* (2013.01); *G01N 30/72* (2013.01); *G01N 30/7233* (2013.01); *G01N 30/86* (2013.01); *H01J 49/005* (2013.01); *H01J 49/0009* (2013.01); *H01J 49/0036* (2013.01)

(58) Field of Classification Search
CPC .......... G01N 30/8631; G01N 30/8637; G01N 30/8665; G01N 30/86; G01N 30/72; G01N 30/7206; G01N 30/7233; H01J 49/0009; H01J 49/0036; H01J 49/005
See application file for complete search history.

(56) References Cited

U.S. PATENT DOCUMENTS

| | | | | |
|---|---|---|---|---|
| 2011/0101215 A1* | 5/2011 | Hirabayashi | ....... | G01N 30/8675 250/282 |
| 2013/0274143 A1* | 10/2013 | Emanuele, II | ...... | H01J 49/0036 506/12 |
| 2014/0179020 A1* | 6/2014 | Wright | .................. | G06F 19/703 436/173 |

FOREIGN PATENT DOCUMENTS

JP   07-083901 A   3/1995

OTHER PUBLICATIONS

International Search Report for PCT/JP2012/059976 dated May 22, 2012.
Extended European search report issued May 28, 2015 in European Patent Application No. 12873982.8.

* cited by examiner

*Primary Examiner* — Jack Berman
(74) *Attorney, Agent, or Firm* — Sughrue Mion, PLLC

(57) ABSTRACT

An equation expressing a previously and experimentally determined relationship between the number of ions and a CV value is stored in a reference CV value calculation data memory. When mass spectrometry is performed for a target sample under measurement conditions including a loop time Tp and a dwell time Td, a chromatogram creator creates a chromatogram based on the analysis result and calculates a peak area value A. A CV-value-related information calculator computes the number X of ions by $X=A\times(Td/Tp)$, and based on the equation stored in the memory, calculates a CV value corresponding to the calculated number of ions. This is a reference CV value containing only statistical dispersion factors for data. This CV value is displayed in such a manner that it can be compared with an actual CV value calculated based on the variance of actually measured peak area values corresponding to a plurality of measurements.

5 Claims, 3 Drawing Sheets

| No. | CONCEN-TRATION [ppt] | DWELL TIME [sec] | LOOP TIME [sec] | AREA VALUE | AVRAGE AREA VALUE | ACTUAL CV VALUE [%] | REFERENCE CV VALUE [%] |
|---|---|---|---|---|---|---|---|
| 1 | 10 | 0.02 | 0.025 | 2526 | 2494 | 7.7 | 5.4 |
| 2 | ↑ | ↑ | ↑ | 2287 | | | |
| 3 | ↑ | ↑ | ↑ | 2667 | | | |
| 4 | 100 | ↑ | ↑ | 15738 | 16675 | 5.0 | 2.4 |
| 5 | ↑ | ↑ | ↑ | 17346 | | | |
| 6 | ↑ | ↑ | ↑ | 16942 | | | |
| 7 | 1000 | ↑ | ↑ | 172578 | 170234 | 1.9 | 0.86 |
| 8 | ↑ | ↑ | ↑ | 171596 | | | |
| 9 | ↑ | ↑ | ↑ | 166528 | | | |

MASS SPECTROMETER

CROSS REFERENCE TO RELATED APPLICATIONS

This application is a National Stage of International Application No. PCT/JP2012/059976 filed Apr. 12, 2012, the contents of all of which are incorporated herein by reference in their entirety.

TECHNICAL FIELD

The present invention relates to a mass spectrometer using a pulse-counting detector as an ion detector, and more specifically, to a mass spectrometer capable of creating a chromatogram by a repetitively-performed mass spectrometry, such as a liquid chromatograph mass spectrometer (LC/MS).

BACKGROUND ART

One important element for evaluating the performance of an analyzing device is data reproducibility. A value frequently used as an index which quantitatively represents the reproducibility is a CV (coefficient of variation) value, which is the standard deviation (STDEV) divided by the average (Average) and multiplied by 100 (the CV value may also be called a relative standard deviation). For example, when a mass spectrometry is performed using a liquid chromatograph mass spectrometer (LC/MS), a calibration curve needs to be previously created based on the result of a measurement of a sample having a known concentration, in which the CV value is extremely important in determining the calibration points. According to a standard set by the U.S. Food and Drug Administration (FDA), the CV value should be 20% or lower at the calibration point corresponding to the limit of quantitation (LOQ) and 15% or lower at the other points.

In general, the CV value of an LC/MS or another type of chromatograph system is calculated from the area values of a plurality of chromatogram peaks (see Patent Literature 1 or other references). However, a CV value calculated based on a chromatogram obtained through one measurement normally does not only contain statistical dispersion factors for the value but also other unstable factors depending on the measurement conditions or the like. Whether or not such unstable factors due to the measurement conditions or the like can be removed so as to acquire stable and highly-reproducible data is critical in evaluating the device as well as in improving the accuracy of the quantitative analysis.

The calculation of the CV value from the area values of chromatogram peaks can be easily achieved using generally available analyzing software products. However, those products are not capable of isolating or identifying unstable factors due to the measurement conditions or the like contained in the calculated CV value. Therefore, it has been difficult for analysis operators to determine whether or not the device is delivering adequately high performance, or whether or not the measurement conditions are appropriate, based on the CV value obtained as a result of an actual measurement.

CITATION LIST

Patent Literature

Patent Literature 1: JP 7-83901 A

SUMMARY OF INVENTION

Technical Problem

The present invention has been developed to solve the previously described problem, and its primary objective is to provide a mass spectrometer which can present, as a reference value, a CV value containing only statistical dispersion factors for the data and thereby allow this value to be compared with an actual CV value in order to facilitate an evaluation of actual measurement data or other tasks. Another objective of the present invention is to provide a mass spectrometer capable of deriving, from a target CV value, appropriate measurement conditions for achieving that CV value.

Solution to Problem

Commonly used ion detectors for mass spectrometers can be roughly divided into two types: a direct-current detector, which measures an average or integral value of an ion current, and a pulse-counting detector, which counts the number of pulses generated by the ions it has received. In general, the former direct-current detector is more commonly used. However, the latter pulse-counting detector, which is advantageous for measuring a trace amount of ions, is often used when the signal intensity is low and when chemical noises are also low. For example, pulse-counting detectors are used in a comparatively large number of LC/MS/MS systems which separate a sample liquid into components by a liquid chromatograph and perform an MS/MS analysis (or tandem analysis) of the components.

In a mass spectrometer using a pulse-counting detector, the signal intensity is represented as the number of ions. Therefore, the number of ions included in a chromatogram peak corresponding to a certain component can be calculated from the area value of the chromatogram peak, the dwell time which is an ion-collecting time allotted for detecting ions originating from that component, and the loop time (or cycle time) which is a period of time required for performing one measurement on each of one or a plurality of ions originating from the measurement target component. Meanwhile, the present inventor has located the fact that the relationship between the number of ions included in a chromatogram peak corresponding to a certain component and the CV value can be approximated by a specific expression, and furthermore, this relationship is independent of the measurement conditions, such as the device or the sample component. This finding has lead the present inventor to the idea of using the aforementioned relationship characteristic of a mass spectrometer employing a pulse-counting detector in order to calculate a CV value which is to serve as a reference.

That is to say, the present invention aimed at solving the previously described problem is a mass spectrometer in which a sample is introduced into an ion source in such a manner that a temporal change in the concentration of one or a plurality of sample components forms a peak, and in which a component in the sample is ionized and the generated ions are detected with a pulse-counting detector after being separated according to their mass-to-charge ratios, the mass spectrometer including:

a) a memory for storing information showing a relational expression obtained based on a result of a preliminary experiment, the relational expression showing a relationship between the number of ions included in one chromatograph peak and a CV value serving as an index of measurement reproducibility; and b) a computation processor for calculating the number of ions from given measurement conditions including a loop time and a dwell time as well as a given value of a chromatogram peak area of a target component, and for calculating a reference CV value by comparing the calculated number of ions with the relational expression based on the information stored in the memory, the loop time being a measurement cycle with which a measurement for sequentially detecting ions originating from one or a plurality of specified components is repeated, the dwell time being a period of time allotted for detecting the ions originating from the target component within the loop time, and the value of the chromatogram peak area being given as a result of an actual or virtual measurement.

Typically, in the mass spectrometer according to the present invention, various kinds of components contained in a sample injected into a mobile phase by a flow injection (FIA) method are introduced into the ion source, or various kinds of components contained in a sample which has been separated into components while passing through a column are introduced into the ion source. The concentration of the sample components thus introduced into the ion source changes with time in such a manner as to show a hill-shaped peak. Accordingly, a hill-shaped peak appears on a total ion chromatogram created by plotting the amount of all the ions with respect to time or a mass chromatogram created by plotting the amount of ions detected at a specific mass-to-charge ratio with respect to time.

In the mass spectrometer according to the present invention, for example, the information showing a relational expression of the number of ions and the CV value stored in the memory can be previously prepared and stored by a device manufacturer based on a result of a preliminary experiment.

In the mass spectrometer according to the present invention, when a mass spectrometry is performed for a target sample under measurement conditions including the loop time and the dwell time, a chromatogram (total ion chromatogram or mass chromatogram) is created based on the analysis result. As already explained, a hill-shaped peak corresponding to the target component appears on the created chromatogram. The computation processor calculates the peak area value of a chromatogram peak which, for example, has been previously specified, and calculates the number X of detected ions by substituting into the following equation (1) the peak area value A as well as the loop time Tp and the dwell time Td given as the measurement conditions.

$$X = A \times (Td/Tp) \quad (1)$$

In a quantitative analysis in an LC/MS or GC/MS, a calibration curve expressing a relationship between the component concentration and the chromatogram peak area value is previously created based on the result of an analysis of a plurality of standard samples having different component concentrations. Taking this into account, it is possible to configure the computation processor so that, when a certain component concentration is specified, the computation processor determines the chromatogram peak area value with reference to the calibration curve and calculates the number X of ions from equation (1) using that peak area value A, the loop time Tp and the dwell time Td.

In any case, after the number X of ions is obtained, the computation processor calculates the CV value by applying the obtained number X of ions in the relational expression based on the information stored in the memory. This CV value is uniquely determined for the number of ions, independent of the measurement conditions. Therefore, for example, when an actual CV value calculated from an average or standard deviation of chromatogram peak areas obtained through a plurality of measurements is displayed, the task of evaluating this actual CV value will be easier if the CV value obtained in the previously described manner is simultaneously displayed as a standard or reference value. It should be noted that a different reference CV value is required for a different component concentration, since the chromatogram peak area value depends on the component concentration, as explained earlier. Accordingly, as one mode of the present invention, the calculated reference CV value and the actual CV value may preferably be displayed in such a manner that the two CV values can be compared for each of a plurality of component concentrations (or for each different calibration point).

In the mass spectrometer according to the present invention, the computation processor may preferably be configured so as to calculate the number of ions for a given CV value by comparing the CV value with the relational expression based on the information stored in the memory. That is to say, the computation processor may be provided with the function of back-calculating the number of ions from the CV value, as opposed to calculating the CV value from the number of ions.

Additionally, the computation processor may be configured so as to determine one of the three parameters of chromatogram peak area value, dwell time and loop time under the condition that the two other parameters are fixed, after the number of ions is calculated from the CV value. With this system, when there is a target CV value, the dwell time, loop time and other measurement conditions necessary for achieving that CV value can be determined In the case where the loop time is calculated under the condition that the dwell time is fixed, the (maximum) number of components that can be subjected to the measurement within each measurement cycle will be calculated from the loop time.

By using the calibration curve, the component concentration can be determined from the chromatogram peak area value. Accordingly, the computation processor may be configured so as to calculate the chromatogram peak area value for a target CV value under the condition that the dwell time and the loop time are determined, and subsequently, to calculate the component concentration corresponding to that chromatogram peak area value. With this system, when there is a certain target CV value, the component concentration necessary for achieving that CV value can also be determined.

Advantageous Effects of the Invention

The mass spectrometer according to the present invention can show an analysis operator a reference CV value which only contains statistical dispersion factors for the value. By comparing this reference CV value and an actual CV value calculated from an average or standard deviation of chromatogram peak areas obtained through a plurality of measurements, the analysis operator can easily make some judgments on the actual measurement data, e.g. whether or not the data are valid. It is also possible to calculate the reference CV value before the measurement is actually performed, using assumed values of the component concentration, the loop time and the dwell time. Furthermore, with the mass spectrometer according to the present invention, the measurement conditions under which a target CV value will be achieved can be easily deduced, such as the loop time, dwell time, number of components that can be subjected to the measurement within each measurement cycle, component concentration or other measurement conditions.

DESCRIPTION OF EMBODIMENTS

Figure 1:
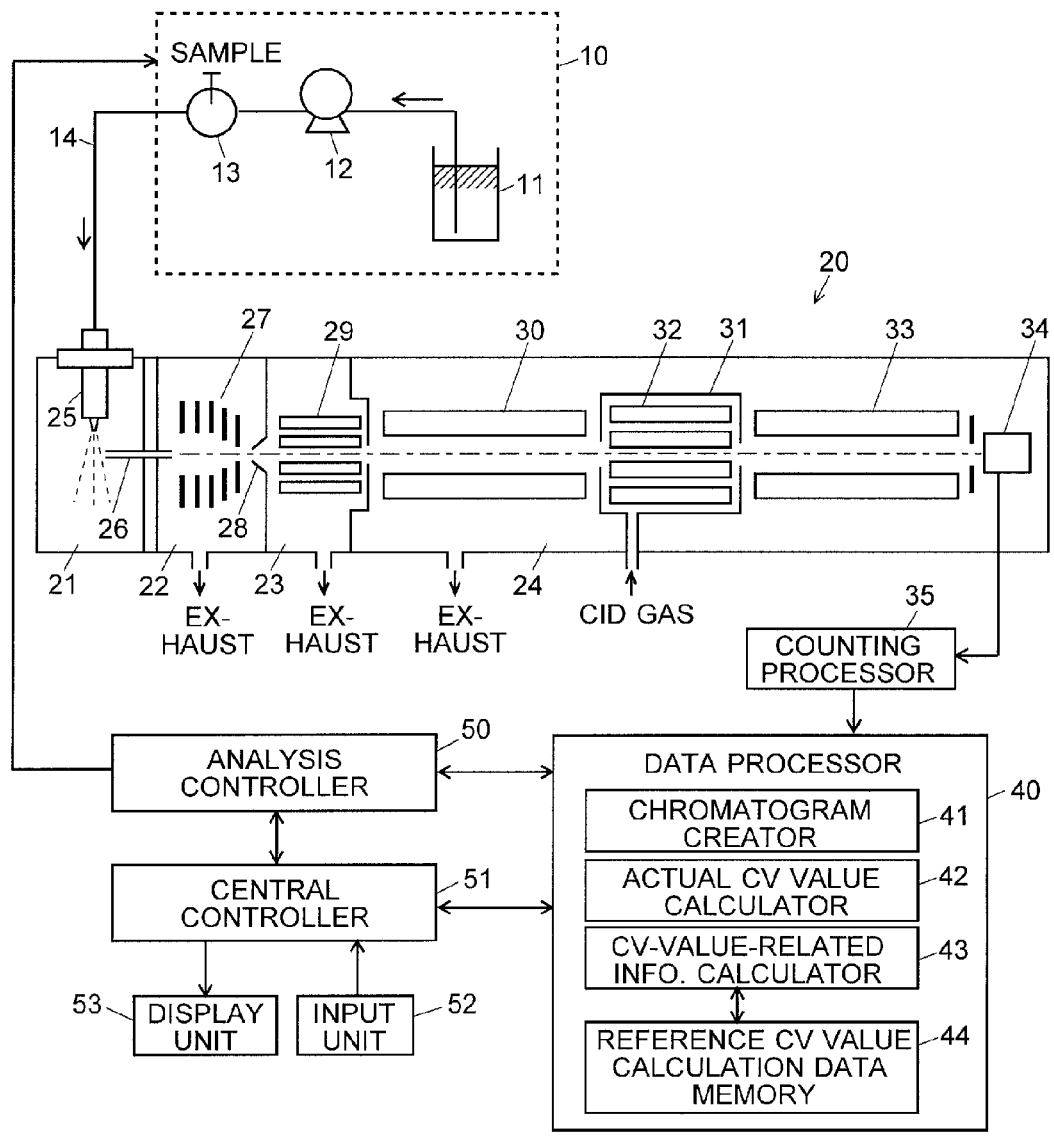
FIG. 1 is a schematic configuration diagram of an LC/MS/MS as one embodiment of the present invention.

An LC/MS/MS as one embodiment of the present invention is hereinafter described with reference to the attached drawings. FIG. 1 is a schematic configuration diagram of the LC/MS/MS of the present embodiment.

An FIA sample introduction unit 10 includes a mobile phase container 11 holding a mobile phase, a pump 12 for drawing the mobile phase and supplying it at a constant flow rate, an injector 13 for injecting a predetermined amount of a prepared sample into the mobile phase, an introduction tube 14 for introducing the sample into a mass spectrometer unit (MS unit) 20, which will be described later. The pump 20 draws the mobile phase from the mobile phase container 11 and supplies it into the introduction tube 14 at a constant flow rate. When a predetermined amount of sample liquid is introduced from the injector 13 into the mobile phase, the sample being carried by the flow of the mobile phase passes through the introduction tube 14, to be introduced into the MS unit 20.

The MS unit 20 has the configuration of a multi-stage differential pumping system including an ionization chamber 21 maintained at approximately atmospheric pressure and a high-vacuum analysis chamber 24 evacuated with a high-performance vacuum pump (not shown), between which first and second intermediate vacuum chambers 22 and 23 are provided having the degree of vacuum increased in a stepwise manner. The ionization chamber 21 has an ESI ionization probe 25 for spraying sample solution while electrically charging this solution. The ionization chamber 21 communicates with the first intermediate vacuum chamber 22 in the next stage through a thin heated capillary 26. The first and second intermediate vacuum chambers 22 and 23 are separated by a skimmer 28 having a small hole at its apex. Ion guides 27 and 29 for transporting ions to the subsequent stage while focusing them are provided in the first and second intermediate vacuum chambers 22 and 23, respectively. The analysis chamber 24 contains a collision cell 31 including a multi-pole ion guide 32, and this cell is sandwiched between a front-stage quadrupole mass filter 30 for separating ions according to their mass to charge ratios and a rear-stage quadrupole mass filter 33 for similarly separating ions according to their mass to charge ratios. An ion detector 34 is also provided in the analysis chamber 24.

In the MS unit 20, when a liquid sample reaches the ESI ionization probe 25, an amount of electrically charged liquid sample is sprayed from the tip of the probe 25. The electrically charged droplets thus sprayed are progressively broken into smaller sizes due to the electrostatic force. During this process, ions originating from the sample components are released. The generated ions are sent through the heated capillary 26 into the first intermediate vacuum chamber 22, where the ions are focused by the ion guide 27 and sent through the small hole at the apex of the skimmer 28 into the second intermediate vacuum chamber 23. In this chamber, the ions originating from the sample components are focused by the ion guide 29 and sent into the analysis chamber 24, where they are introduced into the space extending along the longitudinal axis of the front-stage quadrupole mass filter 30. Naturally, it should be understood that the ionization is not limited to the ESI but may be achieved by APCI or APPI.

When an MS/MS analysis is performed, a predetermined voltage (composed of a radio-frequency voltage and a direct-current voltage superposed on each other) is applied to each of the rod electrodes of the front-stage and rear-stage quadrupole mass filters 30 and 33, while a CID gas is supplied into the collision cell 31 to maintain a predetermined gas pressure inside. Among the various kinds of ions sent into the front-stage quadrupole mass filter 30, only a kind of ion having a specific mass-to-charge ratio corresponding to the voltages applied to the rod electrodes of the front-stage quadrupole mass filter 30 is allowed to pass through this filter 30 and be introduced into the collision cell 31 as a precursor ion. In the collision cell 31, the precursor ion collides with the CID gas and becomes dissociated, generating various kinds of product ions. The generated product ions are introduced into the rear-stage quadrupole mass filter 33, where only a kind of product ion having a specific mass-to-charge ratio corresponding to the voltages applied to the rod electrodes of the rear-stage quadrupole mass filter 33 is allowed to pass through this filter 33, to eventually arrive at and be detected by the ion detector 34.

The ion detector 34, which is a pulse-counting detector, generates pulse signals whose number corresponds to the number of ions received. A counting processor 35 counts those pulse signals and thereby converts them into digital data representing the number of ions received by the ion detector 34. A data processor 40 includes a chromatogram creator 41, an actual CV value calculator 42 and other functional blocks, such as a CV-value-related information calculator 43 and a reference CV value calculation data memory 44 both of which are characteristic components of the present embodiment. An analysis controller 50 controls the operations of the FIA sample introduction unit 10, the MS unit 20 and other sections. A central controller 51, which is provided with an input unit 52 and a display unit 53, is responsible for providing an input/output interface as well as controlling the analysis controller 50 from the higher level. At least a portion of the functions of the central controller 51, the analysis controller 50, the data processor 40 and other sections can be realized by installing a dedicated controlling and processing software program on a multi-purpose personal computer provided as hardware resources and executing this program on the computer.

When a quantitative analysis is performed with the present LC/MS/MS, a multiple reaction monitoring (MRM) measurement mode is very frequently used, in which each of the front-stage and the rear-stage quadrupole mass filters 30 and 33 is individually operated so as to allow only an ion having a specific mass-to-charge ratio to pass through. Therefore, the following description deals with the case of performing the MRM measurement mode to detect a specific product ion originating from a target component. Normally, in an MRM measurement, a plurality of channels each of which corresponds to one combination of the mass-to-charge ratio of the precursor ion and that of the product ion can be set in one measurement. When a plurality of channels are set, every channel is used one time for the measurement within each measurement period (cycle).

Figure 2:
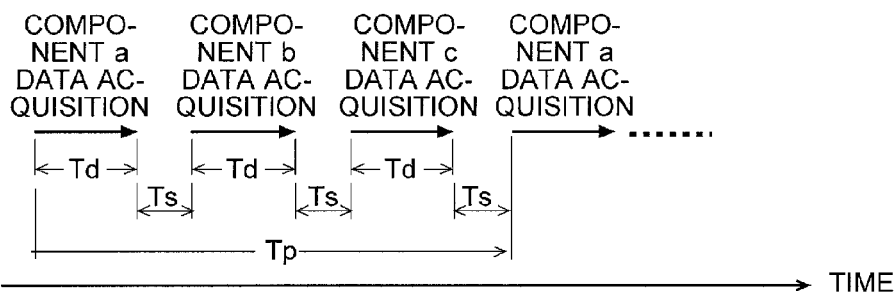
FIG. 2 shows one example of the timing of data acquisition within one measurement cycle in the LC/MS/MS of the present embodiment.

FIG. 2 shows one example of the timing of data acquisition within one measurement cycle in the case where three channels are set (i.e. there are three kinds of different product ions to be detected). The loop time Tp represents the length of one measurement cycle, within which one dwell time Td is allotted for each component to detect product ions originating from this component. The period Ts between one dwell time Td allotted for one component and another dwell time Td allotted for another component is a settling time which is set allowing for a margin required for the voltages applied to the quadrupole mass filters 30 and 33 to settle after being changed so as to vary the mass-to-charge ratios of the ions to be allowed to pass through.

Now, let us take component a for example. The ratio of the length of time within which the product ions originating from component a are detected to the length of one measurement cycle is Td/Tp. The area of the peak on a chromatogram created by the present LC/MS/MS based on the result of the detection of the product ions originating from component a equals the total number of ions counted over a range of time from the beginning to the end of the peak. Accordingly, the relationship of a computationally deduced number X of ions which are included in one chromatogram peak and which contain only statistical dispersion factors, and the three parameters of chromatograph peak area value A, dwell time Td and loop time Tp, can be expressed by the previously noted equation (1):

$$X = A \times (Td/Tp) \quad (1)$$

Figure 4:
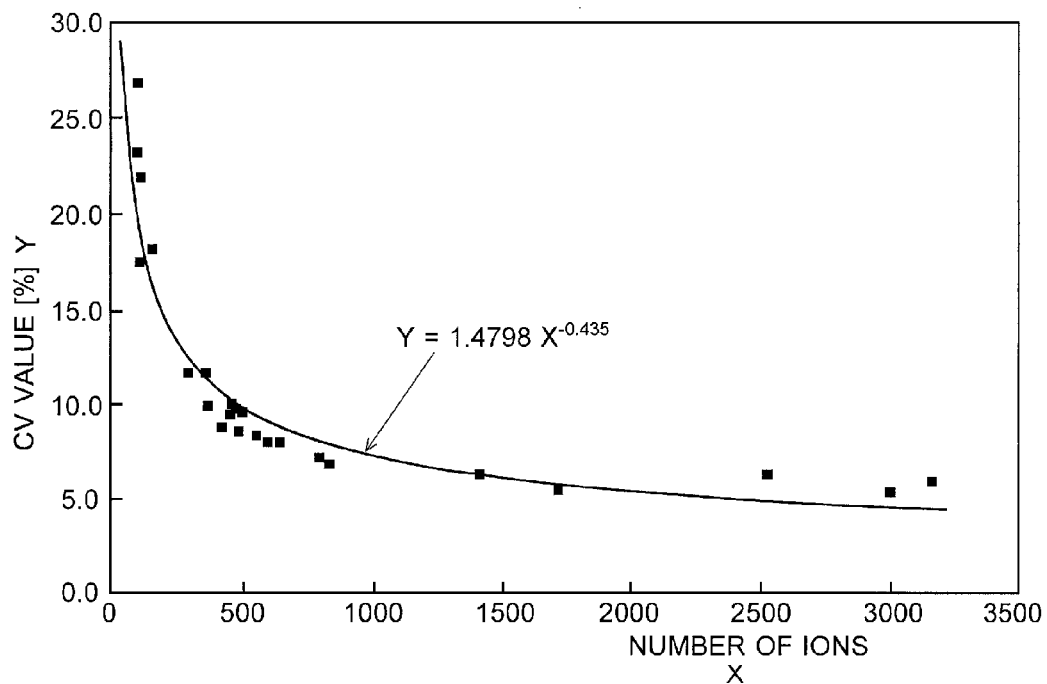
FIG. 4 shows one example of the result of an actual measurement of the number of ions and the CV value as well as a relational expression deduced from that result.

For example, if the measurement conditions of the mass spectrometry are changed, the number of ions detected will change. However, if the number of ions is the same, the CV value must be the same except for statistical factors. FIG. 4 is a graph showing one example of the result of an actual measurement of the relationship between the number X of ions and the CV value Y. The filled squares plotted on this graph represent the relationship between actually measured numbers X of ions and the CV values Y. The distribution of those multiple points thus plotted can be approximated by a curve which satisfies the following equation (2):

$$Y = 1.4798 \times X^{-0.435} \quad (2)$$

In other words, equation (2) is an experimental formula expressing the relationship between the number X of ions and the CV value Y. This experimental formula is dependent on the device configuration but is independent of the measurement conditions. Therefore, the equation can be definitely determined once the device configuration is fixed. Accordingly, in the LC/MS/MS of the present embodiment, it is assumed that the device manufacturer should perform an experiment to determine the relational expression similar to equation (2) and store data representing the relational expression in the reference CV value calculation data memory 44. It is also possible to provide the data processor 40 with a built-in function for allowing users to obtain the experimental formula by following a predetermined procedure so that the experimental formula can be determined after the device is delivered to the users.

A characteristic processing operation related to the CV value in the LC/MS/MS of the present embodiment is hereinafter described.

For ease of explanation, the following description deals with the case of evaluating the reproducibility in creating a calibration curve based on the result of a measurement of three samples containing a known kind of component at different concentrations of 10, 100 and 1000 ppt, respectively. In advance of the measurement, an analysis operator sets the measurement conditions through the input unit 52, including the loop time, dwell time and mass-to-charge ratios to be respectively selected in the quadrupole mass filters 30 and 33.

In the present case, for example, the loop time Tp is set at 0.025 seconds and the dwell time Td at 0.02 seconds, taking into account the condition that only the product ions originating from one component need to be detected within each measurement cycle.

When the analysis operator enters a command for initiating the measurement, a preset sample is injected from the injector 13 into the mobile phase in the FIA sample introduction unit 10 under the control of the analysis controller 50. While passing through the introduction tube 14, the injected sample is temporally spread and reaches the ESI ionization probe 25. Meanwhile, the MS unit 20 is controlled by the analysis controller 50 so as to repeat an MRM measurement with the mass-to-charge ratios set in the aforementioned manner. The chromatogram creator 41 in the data processor 40 creates a chromatogram, on which a peak having a hill-like shape appears according to the change in the number of ions detected with the lapse of time.

Furthermore, the chromatogram creator 41 detects the beginning and ending points of the peak on the chromatogram and calculates the area value of that chromatogram peak.

In the present example, the same measurement is performed three times for each of the samples having the respectively preset component concentrations, and the chromatogram peak area value is calculated for each measurement. More specifically, the measurement is performed three times for each of the three samples having the concentrations of 10, 100 and 1000 ppt, and the chromatogram peak area value is calculated for each measurement. For each concentration, the actual CV value calculator 42 calculates a CV value based on the average of the chromatogram peak area values and the variance (dispersion) of the peak area values obtained through the three measurements. This CV value is a value calculated based on the variance of the actual chromatogram peak area values which reflect the fluctuation and dispersion of the measurement conditions, such as the flow rate of the mobile phase.

Meanwhile, the CV-value-related information calculator 43 computes the number of ions included in the chromatogram peak for each concentration, using equation (1), based on the average of the chromatogram peak area values obtained through the three measurements as well as the loop time Tp and the dwell time Td set as the measurement conditions. The CV-value-related information calculator 43 also computes the CV value corresponding to the calculated number of ions, using equation (2) which is obtained based on the data stored in the reference CV value calculation data memory 44 (see FIG. 3). The CV value thus obtained is independent of the dispersion of the chromatogram peak area values and serves as a reference CV value for evaluating actual CV values calculated by the actual CV value calculator 42. After the actual CV value and the reference CV value are thus obtained for each concentration, the data processor 40 displays, through the central controller 51, the two CV values on the screen of the display unit 53 in such a form that allows the two values to be compared with each other.

Figures 5, 6:
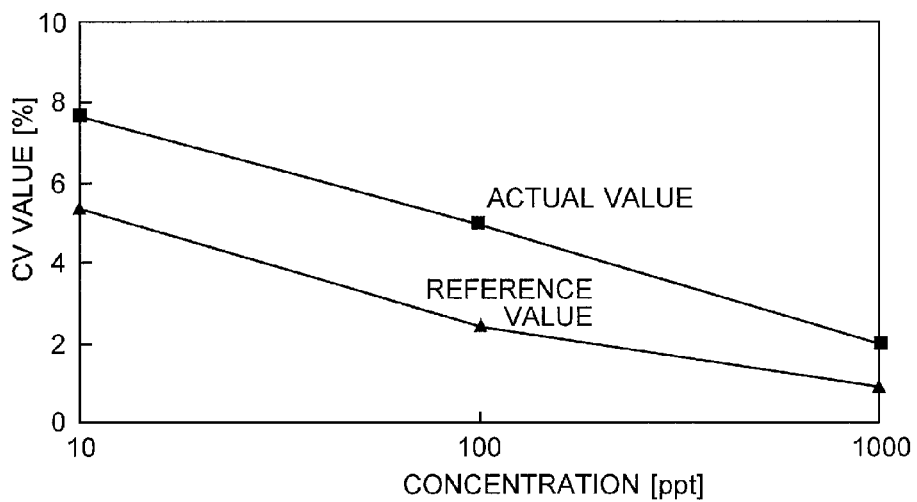
FIG. 5 shows one example of the display form on which the reference CV values and the actual CV values at a plurality of calibration points can be compared.
FIG. 6 shows another example of the display form on which the reference CV values and the actual CV values at a plurality of calibration points can be compared.

FIGS. 5 and 6 show examples of the display form for comparing the reference and actual CV values at each concentration (i.e. at each calibration point). The example of FIG. 5 is in a tabular form, while that of FIG. 6 is in a graph form. The simultaneous display of the reference CV value with the actual CV value allows analysis operators to recognize, for example, that there must be a certain problem in the acquisition of the actual data, such as an inappropriate setting of the measurement conditions, when the actual CV value is abnormally large as compared to the reference CV value.

The CV-value-related information calculator 43 in the LC/MS/MS of the present embodiment can also perform back calculation; i.e. it has the function of calculating and presenting measurement conditions necessary for achieving a desired CV value specified by an analysis operator. As can be understood from FIG. 3, once the CV value Y is determined, the number X of ions can be uniquely determined from equation (2). With the number X of ions thus determined, it is now possible from equation (1) to determine one of the three parameters of chromatogram peak area value A, dwell time Td and loop time Tp under the condition that the two other parameters are fixed. For example, suppose that the dwell time Td and the loop time Tp are fixed. Then, according to equation (1), the number X of ions is proportional to the chromatogram peak area value A, so that it is possible to calculate a chromatogram peak area value A that is minimally required for achieving a desired CV value. The chromatogram peak area value A is dependent on the component concentration of the measurement target sample, and these two parameters are directly related to each other by the calibration curve. Therefore, once the desired CV value is determined, it is possible to determine a component concentration necessary for that CV value.

If the chromatogram peak area value A (i.e. the component concentration) and the loop time Tp are fixed among the three parameters of chromatogram peak area value A, dwell time Td and loop time Tp, once the desired CV value is determined, the dwell time Td that is minimally required for that CV value can be determined. If the chromatogram peak area value A (i.e. the component concentration) and the dwell time Td are fixed, once the desired CV value is determined, the loop time Tp that is minimally required for that CV value can be determined. When the dwell time Td is fixed, the loop time Tp depends on the number of components to be subjected to the measurement within one measurement cycle, which means that the number of components included in one measurement cycle is determined. For example, when the dwell time Td is set at the aforementioned value of 0.02 seconds, if the necessary loop time Tp has been found to be 0.025 seconds, the number of components that can be subjected to the measurement within one measurement cycle is limited to one.

Figure 3:
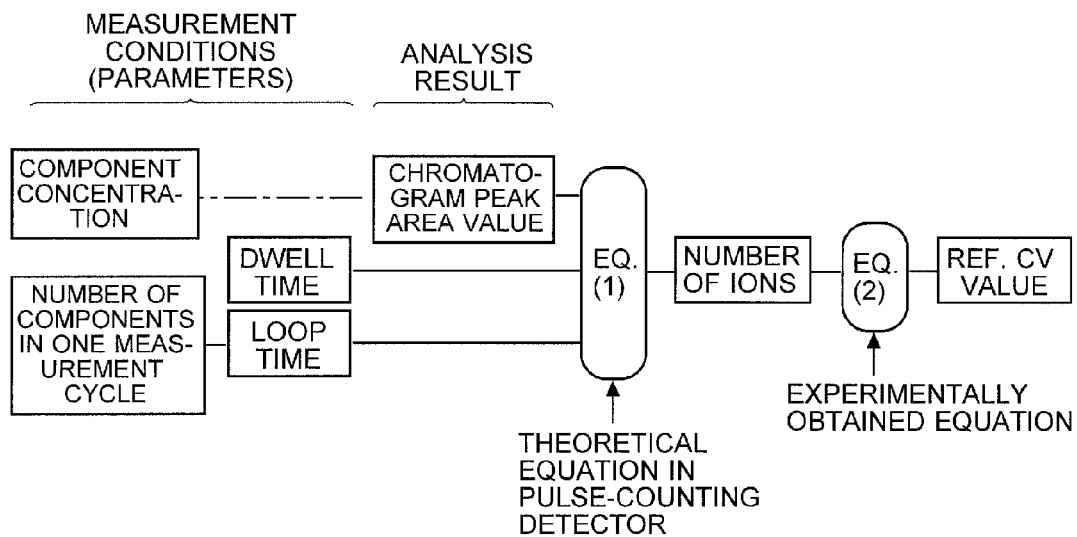
FIG. 3 is a model diagram showing the interrelationship of the various parameters that can be calculated in the LC/MS/MS of the present embodiment.

As described thus far, with the LC/MS/MS of the present embodiment, it is possible to calculate and display the reference CV value to be used as a reference for evaluating an actual CV value obtained as a result of an actual measurement. Conversely, it is also possible to derive measurement conditions (such as the component concentration, the dwell time, the loop time or the number of components to be subjected to the measurement within one measurement cycle) necessary for achieving an arbitrary CV value and to show them to analysis operators. As already explained, the calibration curve represents the relationship between the component concentration and the chromatogram peak area value. Therefore, for example, when a measurement of a sample having a certain component concentration is to be performed under a certain dwell time and a certain loop time, it is possible to calculate a chromatogram peak area value using the calibration curve, and subsequently, to determine the CV value computationally (i.e. without performing an actual measurement) using the relationships of equations (1) and (2) as shown in FIG. 3. In this manner, the best CV value that is expected to be achieved by a measurement can be known before the measurement is actually performed.

It should be noted that the previous embodiment is a mere example of the present invention, and any change, addition or modification appropriately made within the spirit of the present invention will evidently fall within the scope of claims of the present patent application. For example, the device does not need to be an LC/MS/MS as in the previous embodiment but may be an LC/MS or GC/MS, provided that the ion detector is a pulse-counting type. That is to say, the present invention can be applied in various types of mass spectrometers which employ the pulse-counting type ion detector and which are capable of creating a chromatogram.

REFERENCE SIGNS LIST

10 . . . FIA Sample Introduction Unit
11 . . . Mobile Phase Container
12 . . . Pump
13 . . . Injector
14 . . . Introduction Tube
20 . . . MS Unit
21 . . . Ionization Chamber
22 . . . First Intermediate Vacuum Chamber
23 . . . Second Intermediate Vacuum Chamber
24 . . . Analysis Chamber
25 . . . ESI Ionization Probe
26 . . . Heated Capillary
27, 29 . . . Ion Guide
28 . . . Skimmer
30 . . . Front-Stage Quadrupole Mass Filter
31 . . . Collision Cell
32 . . . Multi-Pole Ion Guide
33 . . . Rear-Stage Quadrupole Mass Filter
34 . . . Ion Detector
35 . . . Counting Processor
40 . . . Data Processor
41 . . . Chromatogram Creator
42 . . . Actual CV Value Calculator
43 . . . CV-Value-Related Information Calculator
44 . . . Reference CV Value Calculation Data Memory
50 . . . Analysis Controller
51 . . . Central Controller
52 . . . Input Unit
53 . . . Display Unit

The invention claimed is:

1. A mass spectrometer in which a sample is introduced into an ion source in such a manner that a temporal change in a concentration of one or a plurality of sample components forms a peak, and in which a component in the sample is ionized and the generated ions are detected with a pulse-counting detector after being separated according to their mass-to-charge ratios, the mass spectrometer comprising:
   a) a memory for storing information showing a relational expression obtained based on a result of a preliminary experiment, the relational expression showing a relationship between the number of ions included in one chromatograph peak and a CV value serving as an index of measurement reproducibility; and
   b) a computation processor for calculating the number of ions from given measurement conditions including a loop time and a dwell time as well as a given value of a chromatogram peak area of a target component, and for calculating a reference CV value by comparing the calculated number of ions with the relational expression based on the information stored in the memory, the loop time being a measurement cycle with which a measurement for sequentially detecting ions originating from one or a plurality of specified components is repeated, the dwell time being a period of time allotted for detecting the ions originating from the target component within the loop time, and the value of the chromatogram peak area being given as a result of an actual or virtual measurement.

2. The mass spectrometer according to claim 1, wherein the computation processor has a function of calculating the number of ions for a given CV value by comparing the CV value with the relational expression based on the information stored in the memory.

3. The mass spectrometer according to claim 2, wherein the computation processor has a function of determining one of the three parameters of chromatogram peak area value, dwell time and loop time under a condition that the two other parameters are fixed, after the number of ions is calculated from the CV value.

4. The mass spectrometer according to claim 3, wherein the computation processor has a function of calculating, from the loop time, the number of components that can be subjected to the measurement within each measurement cycle, after the loop time is calculated under a condition that the chromatogram peak area value and the dwell time are fixed.

5. The mass spectrometer according to claim 3, wherein the computation processor has a function of calculating a component concentration using a relationship between the chromatogram peak area value and the component concentration, after the chromatogram peak area value is calculated under a condition that the dwell time and the loop time are fixed.

* * * * *